United States Patent [19]

Salyer

[11] Patent Number: 5,100,267

[45] Date of Patent: Mar. 31, 1992

[54] DISPOSABLE ACETABULAR REAMER CUP

[75] Inventor: Paul E. Salyer, Warsaw, Ind.

[73] Assignee: Othy, Inc., Warsaw, Ind.

[21] Appl. No.: 668,926

[22] Filed: Mar. 13, 1991

[51] Int. Cl.$^5$ .......................... A61B 17/16; B23C 5/12
[52] U.S. Cl. .......................................... 407/54; 407/61; 606/81
[58] Field of Search .................. 407/54, 34, 58, 59, 407/61-63; 606/79-81, 85; 76/116, 21, 101.1, 115; 403/282, 365, 375; 408/204, 703

[56] References Cited

U.S. PATENT DOCUMENTS

| 2,785,673 | 3/1957 | Anderson | 606/81 |
| 4,023,572 | 5/1977 | Weigand et al. | 606/81 |
| 4,072,441 | 2/1978 | LaPointe | 408/204 |
| 4,131,116 | 12/1978 | Hedrick | 408/227 X |
| 4,811,630 | 3/1989 | Salyer | 76/115 |

Primary Examiner—Steven C. Bishop
Attorney, Agent, or Firm—Lundy & Associates

[57] ABSTRACT

A disposable acetabular reamer cup which has a cutting bowl haing a plurality of cutting edges. The cutting bowl has perforations adjoining the cutting edges. The cutting bowl defines an axis of rotation. The cutting bowl has a bottom opening. A polymeric plug is joined to the cutting bowl. The plug is concentric with the axis of rotation. The plug occupies the bottom opening. The plug has a tool driver opening concentric with the axis of rotation.

23 Claims, 1 Drawing Sheet

DISPOSABLE ACETABULAR REAMER CUP

BACKGROUND OF THE INVENTION

The present invention pertains to acetabular reamer cups and more particularly pertains to a disposable acetabular reamer cup.

Acetabular reamers are surgical tools, which are used to cut hemispherical cavities in pelvis bones for the insertion of artificial hip joints. An acetabular reamer is composed of an acetabular reamer cup mounted on a tool driver, which in turn is mounted in the chuck or collet of a portable drill or flexible powered shaft. Acetabular reamer cups have a complex arrangement of precisely shaped cutting surfaces extending outwardly from an essentially hemispherical shell. Acetabular reamer cups are separable from their tool drivers for changing cup size prior to or during surgery, cleaning, and/or sharpening.

Acetabular reamers must be capable of producing cavities with very close tolerances and must also minimize any risk of causing contamination. Acetabular reamer cups have precise dimensions and are light in weight and must fit on an appropriate tool driver with a minimum of free play and must be quick and easy to install and remove without tools. Prior acetabular reamer cups must be cleaned after each use. Thus, the desirability of a disposable reamer cup.

Some previous acetabular reamers have used an open-bottom acetabular reamer cup gripped by the tool driver by means of a flange and slot and an opposed spring-loaded ball catch, like that on a socket wrench or socket driver. This presents a problem in that the catch tends to trap dried blood, which is very difficult to remove during cleaning. An additional problem is that unless tolerances of cups and tool drivers are made very close, at great cost, there is considerable free play between a cup and its tool driver. This increases wear and decreases the precision of the tool.

An alternative acetabular reamer, described in U.S. Pat. No. 4,811.632, utilizes a convex-bottomed acetabular reamer cup having a large central opening complementary in shape to a flange on the tool driver. Since the tool driver also grips the cup with a clamping action, extremely close tolerances are not required to prevent free play between the cup and driver. The convex bottom of the cup eliminates any internal ninety degree angles which could catch contaminants and the large central opening permits easy cleaning. The acetabular reamer cup is, however, complex in shape and expensive and, like all acetabular reamer cups, difficult to resharpen and must be cleaned between uses.

It is therefore highly desirable to provide an improved acetabular reamer cup.

t is also highly desirable to provide an improved acetabular reamer cup which is disposable and fits on a to driver with a minimum of free play.

It is also highly desirable to provide an improved acetabular reamer cup which is disposable and precise in size, light in weight and inexpensive.

it is also highly desirable to provide an improved acetabular reamer cup which is disposable and quick and easy to install and remove from a tool driver without tools.

It is finally highly desirable to provide an improved disposable acetabular reamer cup which meets all of the above desired features.

SUMMARY OF THE INVENTION

It is an object of the invention to provide an improved acetabular reamer cup.

It is another object of the invention to provide an improved acetabular reamer cup which is disposable and fits on a tool driver with a minimum of free play.

It is another object of the invention to provide an improved acetabular reamer cup which is disposable and precise in size, light in weight and inexpensive.

It is another object of the invention to provide an improved acetabular reamer cup which is disposable and quick and easy to install and remove from a tool driver without tools.

t is finally an object of the invention to provide an improved disposable acetabular reamer cup which provides all of the above objects.

In the broader aspects of the invention there is provided a disposable acetabular reamer cup which has a cutting bowl having a plurality of cutting edges. The cutting bowl has perforations adjoining the cutting edges. The cutting bowl defines an axis of rotation. The cutting bowl has a bottom opening. A polymeric plug is joined to the cutting bowl. The plug is concentric with the axis of rotation The plug occupies the bottom opening. The plug has a tool driver opening concentric with the axis of rotation.

BRIEF DESCRIPTION OF THE DRAWINGS

The above mentioned and other features and objects of the invention and the manner of attaining them will become more apparent and the invention itself will be better understood by reference to the following description of an embodiment of the invention taken in conjunction with the accompanying drawings wherein.

DESCRIPTION OF A SPECIFIC EMBODIMENT

Figure 1:
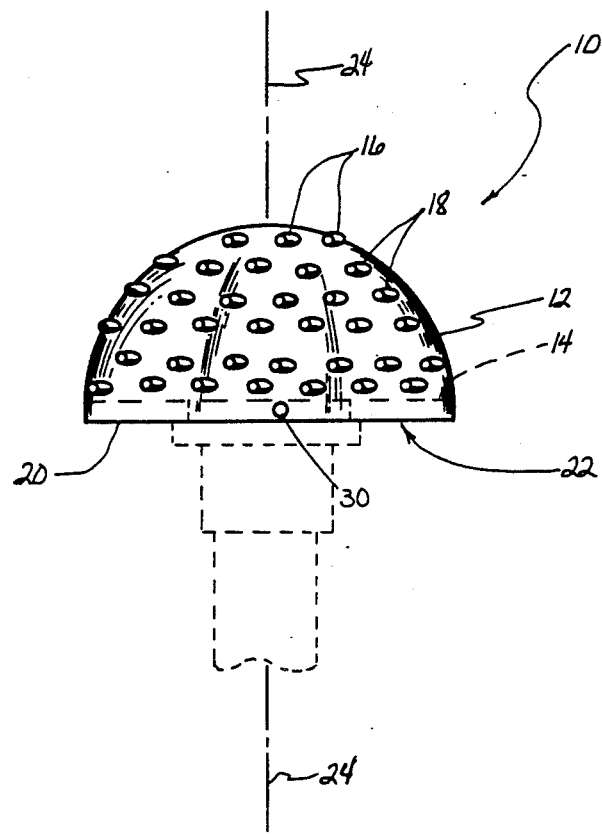
FIG. 1 is a perspective view of an embodiment of the disposable acetabular reamer cup of the invention.

The disposable acetabular reamer cup 10 of the invention has a cutting bowl 2 and a plug 14. Cutting bowl 12 is substantially hemispherical in shape and has a spirally arranged pattern of outwardly extending cutting edges 16 and adjoining perforations 18. Cutting bowl 2 has a periphery 20 surrounding a bottom opening 22. Cutting bowl 12 defines an axis of rotation 24, which is perpendicular to a plane defined by periphery 20. In a particular embodiment, the material of cutting bowl 12 is 19 gauge (0.040") 410 surgical stainless steel, and both the bowl 2 and the cutting edges 16 are formed as disclosed in U.S. Pat. No. 4,811,632, the specification of which is incorporated herein by reference.

Plug 14 occupies bottom opening 22 and is joined to cutting bowl 12. Plug 14 is concentric with axis of rotation 24. Plug 14 defines, in combination with cutting bowl 12, a hollow cup chamber 26. Plug 14 has a tool driver opening 28 concentric with the axis of rotation 24. In a particular embodiment of the invention, plug 14 is circular and fits tightly within cutting bowl opening 22, adjoining periphery 20, and tool driver opening 28 is hexagonal in shape. Tool driver opening 28 is concentric with axis of rotation 24.

Plug 14 is retained in bottom opening 22, in a fixed position, by detents 30 and complementary intrusions 32. Each detent 30 is an inwardly extending portion of cutting bowl 2, which is staked, punched, embedded or driven into the intrusions 32 of plug 14. Plug 14 is joined to cutting bowl 12 solely by detents 30 and intrusions 32 and the friction between the cutting bowl 2 and the plug 14. In a particular embodiment of the invention, two to six equally separated detents 30 positioned adjacent to periphery 20 extend inwardly in a direction radial to axis of rotation 24 to a distance from about 0.020" to about 0.040".

Figure 3:
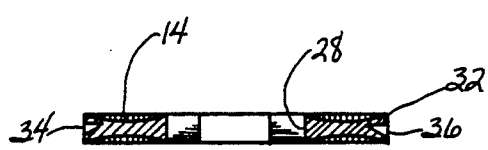
FIG. 3 is a cross-sectional view of one plug of the disposable acetabular reamer cup of the invention taken diametrically.
Figure 4:
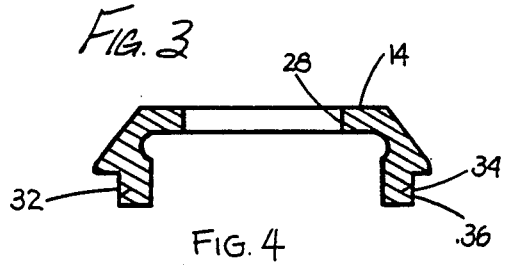
FIG. 4 is a cross-sectional view of another plug of the disposable acetabular reamer cup of the invention like FIG. 3 taken diametrically.

Plug 14 is molded of a polymeric material. In a particular embodiment plug 14 is a disk of a uniform thickness with circular cross-sections taken transversely to its axis. In another particular embodiment, plug 14 may have cross-sections taken axially of a variety of shapes. In one particular embodiment, disk 14 in crosssections taken axially, disk 14 is of uniform thickness. In another particular embodiment disk 14 in crosssections taken axially, is thicker adjacent driver opening 28 and periphery 20. In this particular embodiment, a portion of disk 14 between opening 28 and periphery 20 is "necked" down in cross-section thereby providing easy viewing into the interior of the reamer cup through plug 14 at all times. See FIG. 3. In another particular embodiment, as shown in FIG. 4, plug 14 has a crosssectional shape of a disk with a conical frustum coaxially joined together.

Figure 2:
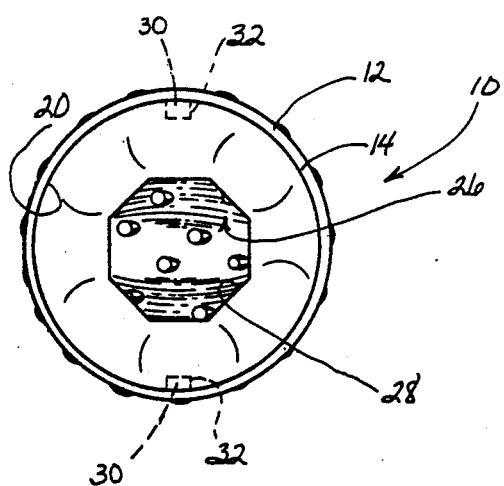
FIG. 2 is a bottom plan view of the disposable acetabular reamer cup of FIG. 1.

Plug 14 is molded so as to form the intrusions 32 in the outer periphery 20. Protrusions may range from two diametrically opposed intrusions to six equally spaced or three pairs of diametrically opposed protrusions in the periphery 20. In a preferred embodiment, each of the protrusions from a top plan view have a rectangular shape with two opposed ninety degree angles as shown in FIG. 2 in dashed lines. The protrusions of this same preferred embodiment, when viewed in crosssections taken axially of plug 14, have a triangular cross-section with a planar sloping wall 34 extending from adjacent the periphery 20 inwardly and a planar orthogonal wall 36 extending generally parallel to the top and bottom surfaces of plug 14. Thus, intrusions 32 of this embodiment are wedge shaped. As shown in FIG. 2, the detents 30 positioned within intrusions 32 substantially fill the intrusions 32.

In a particular embodiment, the plug 14 is formed of polycarbonate material. Plug 14 when in the shape of a disk is approximately ⅛" thick. In all embodiments of the acetabular reamer cup of the invention, each detent 30 is formed by staking, punching or driving the metal of the cutting bowl 2 overlaying the intrusions 32 into the intrusions 32 thereby deforming the metal into the void of the intrusion 32 substantially filling the void of the intrusion 32 and forming a detent of a similar shape to the shape of the intrusion 32.

The polycarbonate material of plug 14 which is strong, lightweight, and transparent, having high temperature and impact resistance. An example of such a material is a polycarbonate sold under the trademark LEXAN by E.I. Dupont de Nemours and Company.

The disposable acetabular reamer cup 10 of the invention is used in the same manner as other acetabular reamer cups, with the exception that because of its relatively low cost, the acetabular reamer cup 10 of the invention may be discarded after a single surgical use rather than being cleaned and reused.

Several embodiments of the disposable acetabular reamer cup of the invention were destructively tested to determine the maximum torque which could be withstood by the reamer cup before failure. Conventionally, these cups are essentially spherical in shape with a radius from about 40mm to about 80mm. Six acetabular reamer cups of the invention, each composed of 410 surgical stainless steel provided with a ⅛" thick disk of LEXAN polycarbonate joined together by four equally separated detents and complementary intrusions as illustrated in the drawings were tested by attaching the same into a tool driver of the type disclosed in U.S. Pat. No. 4,811,632. The tool driver was clamped in a vise whereby the longitudinal axis of the tool driver and the axis of rotation of the acetabular reamer cups were essentially vertical. A ⅛" hexagonal machine nut was welded coaxially of each acetabular reamer cup. A conventional torque wrench was then applied to the nuts and each of the acetabular reamer cups of the invention were torqued until failure. The torque registered at failure was recorded. Half of the acetabular reamer cups tested were torqued in a clockwise direction. The other half of the acetabular reamer cups of the invention were torqued in a counterclockwise direction. The test results are indicated below.

Failure occurred in each case by the plug 14 separating from the bow 12. All of the plugs tested failed between 300 and 342 inch-pounds. The average inch-pounds at failure was 327.33 inch-pounds. The plugs tested failed as follows:

Plug 1 failed at 326 inch-pounds in clockwise rotation
Plug 2 failed at 342 inch-pounds in counterclockwise rotation
Plug 3 failed at 300 inch-pounds in clockwise rotation
Plug 4 failed at 340 inch-pounds in counterclockwise rotation
Plug 5 failed at 336 inch-pounds in clockwise rotation
Plug 6 failed at 320 inch-pounds in counterclockwise rotation The improved acetabular reamer cup provides a disposable reamer cup which fits on a tool driver with a minimum of free play, light in weight, relatively inexpensive and quick and easy to install from a tool driver.

While a specific embodiment of the invention has been shown and described herein for purposes of illustration, the protection afforded by any patent which may issue upon this application is not strictly limited to the disclosed embodiment but rather extends to all structures and arrangements which fall fairly within the scope of the claims which are appended hereto:

WHAT S CLAIMED IS:

1. A disposable acetabular reamer cup comprising a cutting bowl having a plurality of cutting edges, said cutting bowl having perforations adjoining said cutting edges, said cutting bowl defining an axis of rotation, said cutting bowl having a bottom opening coaxial of said bowl, and a transparent plug within said bottom opening and coaxial of said bow, said plug joined to said cutting bowl, said plug having a tool driver opening therein, said opening being coaxial of said bowl.

2. The disposable acetabular reamer cup of claim 1 wherein said cutting bowl has a plurality of inwardly extending detents and said plug has a plurality of complementary inwardly extending intrusions, said plug being gripped by said bowl, said plug being in fixed relation to said bowl.

3. The disposable acetabular reamer cup of claim 2 wherein said detents and intrusions each extend inwardly in a direction radial to said axis of rotation.

4. The disposable acetabular reamer cup of claim 2 wherein said plug is joined to said bowl by said detents and intrusions.

5. The disposable acetabular reamer cup of claim 2 wherein there are from about 2 to about 6 of said detents and intrusions.

6. The disposable acetabular reamer cup of claim 2 wherein said intrusions are wedge shaped with one planar surface being parallel to diameters of said bowl.

7. The disposable acetabular reamer cup of claim 1 wherein said shaft can transmit a torque of more than 300 inch-pounds in a first direction of rotation coaxial with said tool driver boss opening and a torque of more than 300 inch-pounds in a second direction of rotation opposite in handedness to said first direction of rotation.

8. The disposable acetabular reamer cup of claim 1 wherein said tool driver opening is hexagonal.

9. The disposable acetabular reamer cup of claim 1 wherein said tool driver opening is octagonal.

10. The disposable acetabular reamer cup of claim 1 wherein said plug is a disk of polymeric material.

11. A disposable acetabular reamer cup comprising a cutting bowl having a plurality of cutting edges, said cutting bowl being substantially semi-spherical in shape, said cutting bowl having a bottom opening, said cutting bowl having a plurality of inwardly extending detents, said bowl defining an axis of rotation, and a transparent plug within said bottom opening, said plug being gripped by said bowl to said bowl, said plug being coaxial of said bowl, said plug having a tool driver opening, said opening being coaxial of said bowl.

12. The disposable acetabular reamer cup of claim 11 wherein said plug is composed of a polymeric material.

13. The disposable acetabular reamer cup of claim 12 wherein said plug is joined to said bowl solely by said detents and intrusions.

14. The disposable acetabular reamer cup of claim 12 wherein said shaft can transmit a torque of more than 300 inch-pounds in a first direction of rotation coaxial with said tool driver boss opening and a torque of more than 300 inch-pounds in a second direction of rotation opposite in handedness to said first direction of rotation.

15. The disposable acetabular reamer cup of claim 11 wherein said cutting bowl has plurality of inwardly extending detents and said plug has a plurality of complementary inwardly extending intrusions, said disk being gripped by said bowl, said plug being in fixed relation to said bowl.

16. The disposable acetabular reamer cup of claim 15 wherein said detents and intrusions each extend inwardly in a direction radial to said axis of rotation.

17. The disposable acetabular reamer cup of claim 15 wherein said plug is joined to said bowl by said detents and intrusions.

18. The disposable acetabular reamer cup of claim 15 wherein there are from about 2 to about 6 of said detents and intrusions.

19. The disposable acetabular reamer cup of claim 15 wherein said intrusions are wedge shaped with one planar surface being parallel to diameters of said bowl.

20. The disposable acetabular reamer cup of claim 11 wherein said tool driver opening is hexagonal.

21. The disposable acetabular reamer cup of claim 11 wherein said tool driver opening is octagonal.

22. A disposable acetabular reamer cup comprising a cutting bowl having a plurality of cutting edges, said cutting bowl having perforations adjoining said cutting edges, said cutting bowl defining ann axis of rotation, said cutting bowl having a bottom opening coaxial of said bowl, and a plug within said bottom opening and coaxial of said bowl, said plug having a tool driver opening therein, said opening being coaxial of said bowl, said cutting bowl having a plurality of inwardly extending detents and said plug having a plurality of complementary inwardly extending intrusions, said plug being gripped by said bowl, said plug being in fixed relation too said bowl, said detents and intrusions each extending inwardly in a direction radial to said axis of rotation, said plug being joined to said bowl by said detents and intrusions, there being from about 2 to about 6 of said detents and intrusions.

23. A disposable acetabular reamer cup comprising a cutting bowl having a plurality of cutting edges, said cutting bowl being substantially semi-spherical in shape, said cutting bowl having a bottom opening, sad cutting bowl having a plurality of inwardly extending detents, said bowl defining ann axis of rotation, and a plug within said bottom opening, said plug being gripped by said bowl, said plug being coaxial of said bowl, said plug having a tool driver opening, said opening being coaxial of said bowl, said cutting bowl having a plurality of inwardly extending detents and said plug having a plurality of complementary inwardly extending intrusions, said plug being in fixed relation to said bowl, said detents and intrusions each extending inwardly in a direction radial to said axis of rotation, said plug being joined to said bowl by said detents and intrusions, there being from about 2 to about 6 1 of said detents and intrusions.

* * * * *